US006340474B1

(12) United States Patent
Mesko

(10) Patent No.: US 6,340,474 B1
(45) Date of Patent: Jan. 22, 2002

(54) COMPOSITION FOR POTENTIATING A GROWTH HORMONE AND A METHOD FOR PREPARATION OF SAID COMPOSITION

(76) Inventor: Charles A. Mesko, P.O. Box 608, Millersport, OH (US) 43046

( * ) Notice: Subject to any disclaimer, the term of this patent is extended or adjusted under 35 U.S.C. 154(b) by 0 days.

(21) Appl. No.: 09/366,454

(22) Filed: Aug. 3, 1999

(51) Int. Cl.[7] .............................. A61K 9/20; A61K 9/22; A61K 9/28; A61K 47/00; A01N 25/00
(52) U.S. Cl. ....................... 424/464; 424/463; 424/468; 424/474; 514/783
(58) Field of Search ................................. 424/464, 463, 424/468, 474, 195.1; 514/783

(56) References Cited

U.S. PATENT DOCUMENTS

| 4,816,259 A | * | 3/1989 | Matthews et al. | 424/463 |
| 5,332,727 A | | 7/1994 | Birkmayer | 514/52 |
| 5,654,288 A | | 8/1997 | Birkmayer | 514/52 |

OTHER PUBLICATIONS

Sivarajan Ayurvedic drugs and their plant sources p. 67, 155–157 1994.*
Chatterjee and Pakrashi The treatise on Indian medicinal plants vol. 2 p. 102–103, vol. 3 p.128–130 1992.*
Peiper and Anderson, Natural Solutions for Sexual Enhancement pp 66 and 76, 1998.*
Dr. Howard Peiper and Nina Anderson, *Natural Solutions for Sexual Enhancement*, pp. 66 and 76 1998.
Caroline M. Krastek, What's New is Old Again, Whole Foods Magazine, Aug., 1998 pp. 52–59.
Morse Chemical, Inc., San Gabriel, CA, Pharmaceutical/Vitamin/Health Food, Specification Sheet.
Daniel Rudman, M.D. et al., Effects of Human Growth Hormone in Men Over 60 Years Old, The New england Journal of Medicine, vol. 323, No. 1, Jul. 5, 1990.

* cited by examiner

*Primary Examiner*—Thurman K. Page
*Assistant Examiner*—Todd D Ware
(74) *Attorney, Agent, or Firm*—Wood, Herron & Evans, LLP

(57) ABSTRACT

A pharmacologically acceptable growth hormone-potentiating composition for ingestion in a mammal, in a pill form. The composition includes a first herbal extract having an element to synthesize a catecholamine for stimulating release of growth hormone and a second herbal extract including a luteinizing agent which prevents the synthesizing agent of the first herbal extract from breaking down. The pill has an outer surface covered by a protective coating operable to retard acidic degradation of the herbal extracts. The combination of herbal extracts and protective coating result in enhanced uptake into the mammalian system of the synthesizing element of the first herbal extract.

27 Claims, No Drawings

COMPOSITION FOR POTENTIATING A GROWTH HORMONE AND A METHOD FOR PREPARATION OF SAID COMPOSITION

FIELD OF THE INVENTION

The present invention relates generally to a composition for effecting the release of hormones in a mammal and specifically to a composition in capsule form, for ingestion into the human system and absorption in the intestine of the human system, that results in stimulating the release of human growth hormone by the pituitary gland. The composition of the present invention also reduces the incidence of erectile dysfunction in males and enhanced prosexual behavior.

BACKGROUND OF THE INVENTION

Human growth hormone (somatotropin) is a physiological substance produced in the anterior lobe of the pituitary gland of the human system. It is the most abundant hormone produced by the anterior pituitary lobe, accounting for as much as eight to ten percent of the dry weight of the gland. The physiological effects of human growth hormone are macroscopic, extending beyond cellular, chemically mediated events. One example of this is the effect of human growth hormone on whole body growth. Growth hormone effects an increase in tissue and organ weight, which results from an increase in mitosis, cellular hypertrophy, hyperplasia and cellular water. Growth hormone also stimulates the increased uptake of amino acids into cells, resulting in protein synthesis. Growth hormone is responsible for proper growth and development until adulthood and then regulates nearly every organ in the body.

Growth hormone also has prosexual effects, such as enhanced sexual performance and a decrease in the incidence of impotence in males. Studies have suggested that an estimated 70%–80% of cases of erectile dysfunction may be caused by increased levels of prolactin, another hormone released by the pituitary gland. Growth hormone release from the pituitary gland can be associated with a decrease in the release of prolactin.

Growth hormone is synthesized in the acidophilic somatotropes, which are specialized cells located in the anterior of the pituitary gland. Secretion of the growth hormone by the pituitary gland is episodic. The anterior pituitary operates in conjunction with the hypothalamus and adrenal glands as an integrated unit. The large array of physiological factors that effect growth hormone secretion act on the pituitary gland through the hypothalamus. The hypothalamus controls this secretion by causing the release of either growth hormone release stimulating or inhibiting factors. These factors result in the release or retention of human growth hormone by the pituitary gland.

Human growth hormone was first discovered by researchers in the 1920s, and due to its effects on whole body growth, was considered to be a promising therapeutic agent. In 1958, growth hormone extracted from the pituitary glands of cadavers was injected into a growth stunted child at the New England Medical Center in Boston, Mass. As a result the child grew taller and popularity for the use of growth hormone in medical applications grew.

However, one major drawback of the natural growth hormone, is that heat destroys the pituitary extract. Thus, it cannot be pasteurized to eliminate the possibility of disease transmission. Therefore, before the use of growth hormone as a therapeutic agent could become widespread, it either had to be sterilized or a synthetic hormone had to be produced to reduce the potential for transmission of disease.

In 1986, the Eli Lilly Company developed "Humatrope", a manmade growth hormone identical in structure to the actual human growth hormone. Soon after, in 1990, the New England Journal of Medicine released the results of a six month clinical study on human growth hormone administered to a group of men aged 61 to 81. Without exercise, these men lost body fat and wrinkles and gained lean muscle, along with a thickening of the skin and a regeneration of failing liver tissue.

Following the above-noted study, the potential use of human growth hormone for therapeutic and possibly cosmetic benefits caused an increased demand for growth hormone treatments. However, a number of problems are associated with such use. First, cost is a factor. For example, increased levels of growth hormone have been provided through the injection of human growth hormone (natural or synthetic) from a foreign source directly into the human subject. However, such injections are prohibitively expensive, costing anywhere from $1,200 to $3,500 per month.

Additionally, the injections have to be performed in a medical environment under a physician's supervision. This requirement not only adds to the cost of the treatment, but is also inconvenient to the patient's schedule.

Secondly, increasing levels of a foreign growth hormone within a subject also results in negative side effects. For example, in response to the injection of a foreign growth hormone the hypothalamus triggers elevated levels of somatostatin, a growth hormone release inhibitor, which then prompts the pituitary gland of the subject individual to curb the release of its naturally produced growth hormone. Of course, it is undesirable to inhibit the natural release of the growth hormone from the pituitary gland in favor of the synthetic hormone. More particularly, the release of natural growth hormone from the pituitary gland is controlled by negative feedback involving growth hormone releasing and release inhibiting factors. If growth hormone levels are low, the pituitary gland is stimulated by releasing factors in the hypothalamus to increase the release of natural growth hormone. If growth hormone levels are high, the pituitary gland is inhibited from releasing natural growth hormone by the release inhibiting factor, somatostatin, from the hypothalamus. Thus any addition of growth hormone to the human system, whether natural or synthetic, will impact this negative feedback loop, thereby disrupting the balance of growth hormone levels achieved by the tandem operation of hypothalamus and pituitary gland. As a result, the pituitary gland may slow down or even cease production and release of the natural growth hormone, and the normal function of the pituitary gland of the subject is disrupted.

Due to the aforementioned drawbacks with current procedures for increasing growth hormone level within the body, it is desirable to increase growth hormone levels in the human system without negatively affecting the natural production and release of growth hormone by the pituitary gland. It is also desirable to increase growth hormone levels in a manner which does not require physician supervision. It is further desirable that any such composition or method to achieve such objectives be available at a low cost. Finally, it is desirable for any composition to involve a delivery system that protects the components from degradation in order to achieve a heightened efficiency in increasing growth hormone levels in the human system.

SUMMARY OF THE INVENTION

The present invention solves the problems in the prior art and addresses the above objectives by increasing levels of human growth hormone within the human body. The present invention also results in enhancement of prosexual characteristics in the human system. The present invention comprises a synergistic blend of at least two herbal extracts combined with a unique delivery system to produce a very potent and effective growth hormone-potentiating composition. This combination of herbal extracts is provided in pill form to eliminate the need for physician supervision and to reduce costs. Finally, this combination of herbal extracts works in concert with a unique protective coating to enhance uptake levels of the growth hormone potentiator by the human system.

There are several factors which stimulate growth hormone release by the pituitary. One group of releasing factors includes catecholamines, which are amine derivatives of dihydroxybenzene (or catechol), including norepinephrine, epinephrine and dopamine. Upon introduction to the body, the composition of the present invention acts to affect the production of dopamine within the human system.

The presence of dopamine in the human system stimulates the release of growth hormone by the pituitary gland. Levels of dopamine are increased by a first herbal extract of the composition of the present invention which contains dihydroxyphenylalanine (L-dopa). Once introduced into the human system, L-dopa converts to dopamine and stimulates an increase in serum concentration levels of growth hormone. By using dopamine to stimulate the release of the human system's own naturally-occurring growth hormone, the composition of the present invention avoids disrupting the normal function of the pituitary gland through the use of a foreign growth hormone which is a problem with prior at methods and compositions. L-dopa is also an effective inhibitor of the release of the hormone prolactin by the pituitary gland. As previously noted, increased levels of prolactin in the human system are responsible for an estimated 70%–80% of erection failures in males. Therefore, inhibiting prolactin release in accordance with the principles of the invention will limit erection failures in males.

The growth hormone potentiating composition of the present invention includes, in combination with the first herbal extract, a second herbal extract containing a luteinizing agent as an active component. These luteinizing agents may be saponins and/or alkaloids. The combination of the first and second herbal extracts prevents the L-dopa of the first herbal extract from breaking down in the human system and also helps to maintain the presence of dopamine in the human system for an extended period of time. Additionally, the combination of the first and second herbal extracts of the present invention helps to block the release of somatostatin. Somatostatin is a factor that inhibits the release of growth hormone. As the concentration of growth hormone in the human system rises, the hypothalamus releases somatostatin to control growth hormone levels, as part of the negative feedback loop discussed above. Any release of somatostatin operates counter to the benefits of higher concentrations of growth hormone that the present invention provides. Thus, by blocking the release of somatostatin, the combination of herbal extracts of the present invention maximizes levels of growth hormone in the human system.

In another embodiment of the invention, the composition includes at least two additional components which aid particularly in the enhancement of prosexual behavior in an individual. These include a third herbal extract that, in the inventor's experience, ameliorates problems of erectile dysfunction in males, and an herb that dilates the blood vessels in the human system. Although increased levels of human growth hormone itself result in enhanced prosexual characteristics and behavior, the inventor has found that the particular combination of the embodiment including the third herbal extract and herb for dilating blood vessels has a particular effect in maximizing the enhancement of prosexual characteristics in the human system.

The composition of the present invention is provided in an ingestable, capsule form. In this manner the composition addresses several drawbacks associated with prior art treatments involving the injection of growth hormone. For example, by eliminating the need for injection treatments, the present invention eliminates the need for physician supervision. This results in a reduction of inconvenience for the patient who, in receiving injections, had to manipulate schedules to include a doctor's appointment and had to endure what many patients consider to be discomforting: a needle injection. By providing the composition of the present invention in capsule form, the high costs of treatment associated with injection treatments are likewise reduced.

In accordance with another aspect of the present invention, the compositions include a protective coating which operates to retard acidic degradation of the herbal extracts prior to their absorption into the human system. L-dopa is a very unstable compound which breaks down quickly when in the presence of stomach acid. Prior to the ingestable capsule of the present invention, the L-dopa content of ingestable compositions used to potentiate the natural growth hormone of the pituitary gland was rapidly degraded by acid in the stomach. Therefore, the ingestable capsule is coated with an acid stable protective coating so that the first and second herbal extracts pass through the stomach environment without degradation of the L-dopa and proceed to subsequent absorption by the intestine. The ingestable capsule of the present invention reduces the problem of premature stomach degradation with a unique tablet coating comprising, in one embodiment, a food grade shellac and ethocel (the ethyl ether of cellulose) which shields the herbal extracts of the composition, and thus the L-dopa.

DETAILED DESCRIPTION OF SPECIFIC EMBODIMENTS

The ingestable human growth hormone potentiator of one embodiment of the present invention comprises a pharmacologically acceptable composition having a first herbal extract including an element for synthesizing a catecholamine, a second herbal extract having at least one active component comprising a luteinizing agent, and a protective coating which operates to retard acidic degradation of the herbal extracts and their components prior to their absorption through the intestinal wall and into the bloodstream of a mammal. The first and second herbal extracts are present in an amount effective to potentiate a growth hormone.

The first herbal extract of an embodiment of the composition of the present invention is an extract of the herb *Mucuna Pruriens*. *Mucuna Pruriens* contains the hydroxylated amino acid dihydroxyphenylalanine (L-dopa) and is especially useful in the composition of the present invention in that the percentage of L-dopa found in *Mucuna Pruriens* is unusually high as compared to the L-dopa concentration in other herbs. The extraction process further increases the concentration of L-dopa. The final amount of L-dopa in the *Mucuna Pruriens* extract used in the composition is at least about twenty percent by volume.

L-dopa is the active element in the composition of the present invention in stimulating the release of natural growth hormone by the pituitary gland. L-dopa is a product of the hydroxylation of the amino acid tyrosine by tyrosine hydroxylase to produce dihydroxyphenylalanine (L-dopa). Once L-dopa has been absorbed through the intestinal wall into the blood stream, it crosses the blood-brain barrier where it is then decarboxylated by the enzyme L-aromatic amino acid decarboxylase to produce dopamine, a growth hormone releasing factor. The dopamine then acts upon the hypothalamus and pituitary gland to stimulate an increase in serum concentration levels of natural human growth hormone.

The second herbal extract used in combination with the first herbal extract in one embodiment of the composition of the present invention is an extract of *Tribulus L. Terrestris*. *Tribulus L. Terrestris* is present in the composition in both herb and extract form. This component contains saponins and alkaloids which function as luteinizing agents to prevent the L-dopa of the *Mucuna Pruriens* extract from degrading within the human system before crossing the blood-brain barrier to convert to dopamine by the aforementioned decarboxylation process.

The *Tribulus L. Terrestris* has additional functions when operating in combination with *Mucuna Pruriens* extract in accordance with the principles of the present invention. The combination of the herbal extracts *Mucuna Pruriens* and *Tribulus L. Terrestris* results in improved levels of uptake of L-dopa by the human system. The two extracts operating in concert in the inventive combination also inhibit the release of somatostatin. As previously discussed, somatostatin is a growth hormone release inhibiting factor found in the hypothalamus. Somatostatin blocks the release of natural growth hormone by the pituitary gland. By inhibiting the release of somatostatin, the combination of herbal extracts of the present invention maintains the presence of dopamine in the human system for an extended period of time. These increased levels of dopamine stimulate an increase in the release of natural growth hormone by the pituitary gland. The operation of *Mucuna Pruriens* extract and *Tribulus L. Terrestris* in combination thus maximizes serum concentration levels of natural human growth hormone in the human system.

In another embodiment of the invention, the composition further includes a third herbal extract for acting in concert with the first and second herbal extracts to enhance prosexual characteristics in an individual, and an herb for dilating blood vessels in the human system.

In this embodiment of the invention, the third herbal extract is used in combination with the first and second herbal extracts. Particularly, an extract of the herb *Muira Puama* is combined into the composition. In the experience of the inventor, the inclusion of *Muira Puama* extract reduces the incidence of erectile dysfunction in males.

Another embodiment of the invention additionally includes the herb Horny Goat Weed. Horny Goat Weed lowers the blood pressure by dilating the blood vessels of the body. Although human growth hormone by itself enhances prosexual characteristics in mammals, the addition of *Muira Puama* extract and Horny Goat Weed to the combination of *Mucuna Pruriens* and *Tribulus L. Terrestris* results in a further increase of such prosexual characteristics. Although the exact physiological function of *Muira Puama* extract is unknown, it has been the experience of the inventor that the inclusion of *Muira Puama* with extracts of *Mucuma Pruriens* and *Tribulus L. Terrestris* results in increasing the prosexual function of the combination of the present invention.

Another aspect of the present invention reduces the cost of treatments and eliminates the need for physician supervision during treatment. In accordance with that aspect, the composition of the present invention may be formed into ingestable capsules, tablets, micro tablets or micro pellets by processes known in the art of pill manufacturing. Capsules may be formed by blending the component herbal extracts and subsequently filling capsules with the extract mixture using conventional automatic filling equipment. Tablets may be formed either by direct compression of components or by granulation followed by compression. Micro tablets may be formed by compressing powdered or granulated components into small diameter tablets. In one embodiment of the present invention, the human growth hormone potentiating composition is provided in capsule form. In forming the two herbal extracts into a capsule form in one embodiment, the component ingredients are present in an amount of approximately 250 milligrams of *Mucuna Pruriens* extract containing approximately 20 percent L-dopa and approximately 125 milligrams of *Tribulus L. Terrestris*.

The composition of another embodiment of the invention including a third herbal extract of *Muira Puama* and an herb, Horny Goat Weed, may also be formed into ingestable capsules, tablets, micro tablets or micro pellets with the preferred form being capsule form.

The inventive composition is covered with a unique protective coating in accordance with another aspect of the invention. The coating is used to prevent acidic degradation of the components of the composition. This coating, in one embodiment, includes a food grade shellac and the ethyl ether of cellulose (ethocel). The shellac is a regular bleached food grade shellac with not more than approximately 5.5 percent wax content. One such suitable shellac is available from Morse Chemical, Incorporated. Ethocel is prepared from wood pulp or chemical cotton by treatment with alkali and ethylation of the alkali cellulose with ethyl chloride. Commercial ethyl cellulose has an ethoxy content of 43 to 50 percent. In accordance with one embodiment of the invention, the food grade shellac and ethocel are added to the exterior surface of the capsule as a laquer or coating by applying six coats of food grade shellac and six coats of ethocel. This amount of coating prevents the capsule from disintegrating in the normal human stomach environment for approximately three hours. As such, the L-dopa is prevented from degradation by stomach acid and is retained for absorption through the intestinal wall and into the bloodstream of the human system. The composition of another embodiment of the present invention including the third herbal extract of *Muira Puama* and the herb Horny Goat Weed is enveloped by the same protective coating.

While the present invention has been illustrated by a description of various embodiments and while these embodiments have been described in considerable detail, it is not the intention of the applicants to restrict or in any way limit the scope of the appended claims to such detail. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit or scope of applicant's general inventive concept.

What is claimed is:

1. A pharmaceutically acceptable growth hormone-potentiating composition for ingestion in a mammal comprising:

*Mucuna Pruriens* including an element for synthesizing a catecholamine;

*Tribulus L. Terrestris* having an active component comprising a luteinizing agent; and a protective coating operable for retarding acidic degradation of said *Mucuna Pruriens* and said *Tribulus L. Terrestris* prior to absorption by said mammal.

2. The composition of claim 1 wherein said element of said *Mucuna pruriens* is a hydroxylated amino acid.

3. The composition of claim 2 wherein said hydroxylated amino acid is L-dopa.

4. The composition of claim 1 wherein said catecholamine to be synthesized is dopamine.

5. The composition of claim 3 wherein said L-dopa is present in said *Mucuna pruriens* in an amount of at least about twenty percent by volume.

6. The composition of claim 1 wherein said element for synthesizing a catecholamine is L-dopa, said L-dopa operable to stimulate said mammal to synthesize dopamine, and wherein said *Tribulus L. terrestris* is operable to prevent L-dopa from degrading in the mammal, thereby enhancing dopamine uptake in the mammal.

7. The composition of claim 1 further comprising an extract for enhancing prosexual characteristics in a mammal.

8. The composition of claim 7 wherein said herbal extract is an extract of *Muira puama*.

9. The composition of claim 7 further comprising an herb for dilating blood vessels in a mammal.

10. The composition of claim 9 wherein said herb is Horny Goat Weed.

11. The composition of claim 1 wherein said protective coating for retarding acidic degradation of said *Mucuna pruriens* and said *Tribulus L. terrestris* covers said outer surface of said pill.

12. The composition of claim 1 wherein said protective coating includes a food grade shellac.

13. The composition of claim 1 wherein said protective coating includes an ethyl ether of cellulose.

14. The composition of claim 11 wherein said protective coating is operable to prevent dissolution by stomach acid of said *Mucuna pruriens* and said *Tribulus L. terrestris* for at least three hours in said mammal.

15. A method of preparing a pharmaceutically acceptable growth hormone-potentiating composition for ingestion in a mammal, comprising the steps of:

providing a pill comprising *Mucuna pruriens* and *Tribulus L. terrestris*, *Mucuna pruriens,* said *Mucuna pruriens* including an element for synthesizing a catecholamine and said *Tribulus L. terrestris* having an active component comprising a luteinizing agent, said pill further having an outer surface; and coating said pill with a protective substance operable to retard acidic degradation of said *Mucuna pruriens* and said *Tribulus L. terrestris* prior to absorption by said mammal.

16. The method of claim 15 Wherein said element of said *Mucuna pruriens* is a hydroxylated amino acid.

17. The method of claim 16 wherein said hydroxylated amino acid is L-dopa.

18. The method of claim 17 wherein said catecholamine to be synthesized is dopamine.

19. The method of claim 17 wherein said L-dopa is present in said *Mucuna pruriens* in an amount of at least twenty percent by volume.

20. The method of claim 15 wherein said element for synthesizing a catecholamine is L-dopa, said L-dopa operable to stimulate said mammal to synthesize dopamine, and wherein said *Tribulus L. terrestris* is operable to prevent L-dopa from degrading in the mammal, thereby enhancing dopamine uptake in the mammal.

21. The method of claim 15 wherein said pill further comprises an herbal extract for enhancing prosexual characteristics in a mammal.

22. The method of claim 21 wherein said herbal extract is an extract of *Muira puama*.

23. The method of claim 21 wherein said pill further comprises an herb for dilating blood vessels in a mammal.

24. The method of claim 23 wherein said herb is Horny Goat Weed.

25. The method of claim 15 wherein said protective substance for retarding acidic degradation of said *Mucuna pruriens* and said *Tribulus L. terrestris* covers said outer surface of said pill.

26. The method of claim 15 wherein said protective substance includes a food grade shellac.

27. The method of claim 15 wherein said protective substance includes an ethyl ether of cellulose.

\* \* \* \* \*

UNITED STATES PATENT AND TRADEMARK OFFICE
CERTIFICATE OF CORRECTION

PATENT NO. : 6,340,474 B1
DATED : January 22, 2002
INVENTOR(S) : Charles A. Mesko It is certified that error appears in the above-identified patent and that said Letters Patent is hereby corrected as shown below:

Column 1,
Lines 13-14, "erectile dysfunction in males and enhanced prosexual behavior" should be -- erectile dysfunction in males and enhances prosexual behavior --.

Column 3,
Line 31, "at" should be -- art --.

Column 6,
Line 53, "applicants" should be -- applicant --.

Column 7,
Lines 7 and 13, "Mucuna pruriens" should be -- Mucuna Pruriens --.
Line 18, "Tribulus L. terrestris" should be -- Tribulus L. Terrestris --.
Line 24, "Muira puama" should be -- Muira Puama --.
Line 31, "Mucuna pruriens and said Tribulus L. terrestris" should be
-- Mucuna Pruriens and said Tribulus L. Terrestris --.
Line 39, "Mucuna pruriens and said Tribulus L. terrestris" should be
-- Mucuna Pruriens and said Tribulus L. Terrestris --.

Column 8,
Lines 1-4, "Mucuna pruriens and Tribulus L. terrestris, Mucuna pruriens, said Mucuna pruriens including an element for synthesizing a catecholamine and said Tribulus L. terrestris" should be -- Mucuna Pruriens and Tribulus L. Terrestris, said Mucuna Pruriens including an element for synthesizing a catecholamine and said
Tribulus L. Terrestris --.
Lines 8-9, "Mucuna pruriens and said Tribulus L. terrestris prior to absorption" should be -- Mucuna Pruriens and said Tribulus L. Terrestris prior to absorption --.
Line 11, "of claim Wherein" should be -- of claim 15 wherein --.
Lines 12 and 17, "Mucuna pruriens" should be -- Mucuna Pruriens --.

UNITED STATES PATENT AND TRADEMARK OFFICE
CERTIFICATE OF CORRECTION

PATENT NO.   : 6,340,474 B1
DATED        : January 22, 2002
INVENTOR(S)  : Charles A. Mesko It is certified that error appears in the above-identified patent and that said Letters Patent is hereby corrected as shown below:

<u>Column 8 cont'd,</u>
Line 22, "Tribulus L. terrestris" should be -- Tribulus L. Terrestris --.
Line 29, "Muira puama" should be -- Muira Puama --.
Line 36, "Mucuna pruriens and said Tribulus L. terrestris" should be
-- Mucuna Pruriens and said Tribulus L. Terrestris --.

Signed and Sealed this

Third Day of June, 2003

JAMES E. ROGAN
*Director of the United States Patent and Trademark Office*